(12) United States Patent
Yoon et al.

(10) Patent No.: US 6,571,864 B1
(45) Date of Patent: Jun. 3, 2003

(54) ANTIBACTERIAL AND ANTIFUNGAL ALUMINUM ALLOY FIN MATERIAL AND A HEAT EXCHANGER PROVIDED THEREWITH FOR USE IN AN AIR CONDITIONER

(75) Inventors: Baeg Yoon, Suwon (KR); Hyun-yeon Park, Suwon (KR); Young-saeng Kim, Inchon (KR); Hwan-young Park, Suwon (KR)

(73) Assignee: Samsung Electronics Co., Ltd., Suwon (KR)

( * ) Notice: Subject to any disclaimer, the term of this patent is extended or adjusted under 35 U.S.C. 154(b) by 0 days.

(21) Appl. No.: 09/301,071

(22) Filed: Apr. 28, 1999

(30) Foreign Application Priority Data

Dec. 4, 1998 (KR) .......................... 1998-53527

(51) Int. Cl.$^7$ .......................... F28F 13/18; B32B 15/10; B32B 27/00; B32B 15/08
(52) U.S. Cl. .................. 165/133; 29/890.03; 428/650; 428/148; 428/425.8; 428/461
(58) Field of Search .............................. 428/416, 425.8, 428/461, 654, 553, 650, 148; 165/133, 134.1, DIG. 513; 29/890.03, 890.054

(56) References Cited

U.S. PATENT DOCUMENTS

| 4,460,369 A | * | 7/1984 | Seymour | .................... 604/897 |
| 5,376,411 A | * | 12/1994 | Nishishita | .................... 427/379 |
| 5,399,192 A | * | 3/1995 | Yamasoe | .................... 106/186 |
| 5,478,872 A | * | 12/1995 | Yamasoe et al. | .............. 524/45 |
| 5,538,078 A | * | 7/1996 | Mizuno et al. | .............. 165/133 |

FOREIGN PATENT DOCUMENTS

| JP | 60267812 A | * | 11/1985 |
| JP | 03026381 A | * | 2/1991 |
| JP | 2000028286 A | * | 1/2000 |

* cited by examiner

*Primary Examiner*—Paul Thibodeau
*Assistant Examiner*—Kevin R. Kruer
(74) *Attorney, Agent, or Firm*—Robert E. Bushnell, Esq.

(57) ABSTRACT

Fin material for a heat exchanger, which comprises: a fin material; a water-based resin paint coated on said fin material surface; a hydrophilic coated on said paint coating; and, antibacterial and antifungal powders fixed by said hydrophilic coating and paint coating, wherein the half or less portion of respective powders are exposed to the outside of the hydrophilic coated film so that the properties of said powders can be retained for a sustained period of time and heat exchanger for air conditioner provided therewith.

3 Claims, 1 Drawing Sheet

ANTIBACTERIAL AND ANTIFUNGAL ALUMINUM ALLOY FIN MATERIAL AND A HEAT EXCHANGER PROVIDED THEREWITH FOR USE IN AN AIR CONDITIONER

BACKGROUND OF THE INVENTION

1) Field of Invention

The present invention relates to aluminum alloy fin material and a heat exchanger for use in an air conditioner, more specifically, an antibacterial and antifungal aluminum alloy fin material and a heat exchanger provided therewith for use in an air conditioner.

2) Description of the Prior Art

Generally, a finned tube heat exchanger is used as a heat exchanger for use in an air conditioner. A finned tube heat exchanger is composed of aluminum fins(hereinafter referred to as "fins") and round copper pipes(hereinafter referred to as "copper pipes"). Refrigerant fluid pass in the copper pipes which are closely adhered to the fins therein and an air flow pass among the fins in the direction perpendicular to the fluid When such heat exchanger is used as an indoor evaporator, the refrigerant fluid cooled to 8° C. flows in the copper pipes, and the inflow of the air having the temperature of 20° C. or higher causes a rise in the relative humidity among the fins.

That is, though the temperature of the surfaces of the fins is maintained at around 10° C., it falls below the dew point of the incoming air, and thus drops of water adhere to the surfaces of the fins.

The surfaces of fins in the heat exchanger serve as a good habitat for bacteria and fungi, due to their large area and the humid condition therein. This, therefore, results in such a problem that the air conditioner in operation gives out a bad odor of fungi.

Meanwhile, heat exchanger efficiency is determined by the amount of flow of air. When a heat exchanger serves as an evaporator, drops of water adhere to the surfaces of the fins as described above. Remaining water drops cause increased resistance to the flow of air, thereby reducing the amount of flow of air and entailing decreased efficiencies of not only the heat exchanger but also the air conditioner.

Accordingly, it is important to reduce the resistance to the air flow in view of air conditioner efficiency. Usually, hydrophilic coating film is formed on the fins in order to reduce the resistance. By using such hydrophilic fins, the remaining water on the fin forms a uniform film and the resistance to the air flow is lowered, compared with uncoated fins. Sustaining the hydrophilic property for a long time is therefore highly related to the enhancement of the air conditioner efficiency. In addition, it is also required that the surfaces of the fins are corrosion-resistant enough to maintain such hydrophilic property for a long time.

As described above, it is important how to keep the hydrophilic property and the corrosion resistance for imparting the antifungal and antibacterial properties, to the air conditioner with a heat exchanger provided with hydrophilic fins.

In order to give the antifungal and antibacterial properties, methods of adding antibacterial agent and antifungal agent to a conventional hydrophilic coating system have been used. For example, Unexamined Japanese Patent Publication Hei 1-240688 discloses a heat exchanger Al fin material with antifungal surface, obtained by forming corrosion resistant coating film on the plate surface of Al alloy and then hydrophilic coating containing benzimidazolic compounds. And also Unexamined Japanese Patent Publication Hei. 2-101395 discloses an Al fin material which exhibits its antifungal effect as soon as fungi are generated by the deposition of water, obtained by adding a rapid-acting antifungal agent into the hydrophilic coating film and by adding a delayed-acting antifungal agent into the corrosion resistant coating film.

The common object of the above technologies is to give the fin surfaces a hydrophilic property and also the antibacterial and antifungal properties, keeping the hydrophilic property of the surface.

The above prior arts disclose the method of incorporating antibacterial and antifungal agents into the coating film treated on the fin surfaces. However, in the case of Japanese Patent Unexamined Publication No. 1-240688 where the antibacterial and the antifungal agents are incorporated into the hydrophilic coating film, it is difficult to preserve the hydrophilic property or the antibacterial and antifungal properties at a high level for a long period.

That is, addition of the antibacterial and antifungal agents with high hydrophobic property results in the deterioration of the hydrophilic property, while antibacterial and antifungal agent with high hydrophilic property are easily eluted in dewing water and thus not able to exhibit their properties for a long period.

On the other hand, in the case of Japanese Unexamined Patent Publication No. 2-101395, the delayed-acting antibiotics in hydrophilic coating exhibits their effects after the antibacterial and the antifungal agents in the corrosion resistant coating are eluted into the dewing water and the desired properties therefore can be sustained for a long time. However, when the delayed-acting antibiotics exhibits their effect, the hydrophilic coating has already flowed out and thus sustaining the hydrophilic property for a long time at a high level cannot be obtained.

SUMMARY OF THE INVENTION

It is the purpose of the present invention to provide an aluminum alloy fin material whose hydrophilic property and antibacterial and antifungal properties are sustained for a long period at a high level, and a heat exchanger for air conditioner provided therewith.

These and other objects may be attained aluminum-alloy fin material with antibacterial and antifungal properties. This material may be arranged with a first film with average dry thickness of 0.8–2.2 microns, such as a water-soluble resin paint containing 1–30 wt % of (A) bis-(2-pyridylthio)-zinc-1,1'-dioxide particles based on the total solids in the composition of the paint, 40 vol % or more of bis-(2-pyridylthio)-zinc-1,1'-dioxide particles being 1–10 microns in diameter, and a second film with average dry thickness of 0.1–0.6 microns, formed on the first film. The second film may be formed from a mixed aqueous solution such as (P1) vinyl resin with secondary alcoholic structure or derivative thereof, (P2) a water soluble acrylic resin with sulfonic acid group or salt(s) thereof and (B) blocked isocyanate compound, in the ratio of(P1):(P2)=1:8 by weight for solids or in the range of ((P1)+(P2)):(B)=94:6 to 86:14 by wt % for solids.

DETAILED DESCRIPTION OF THE INVENTION

Figure 1:
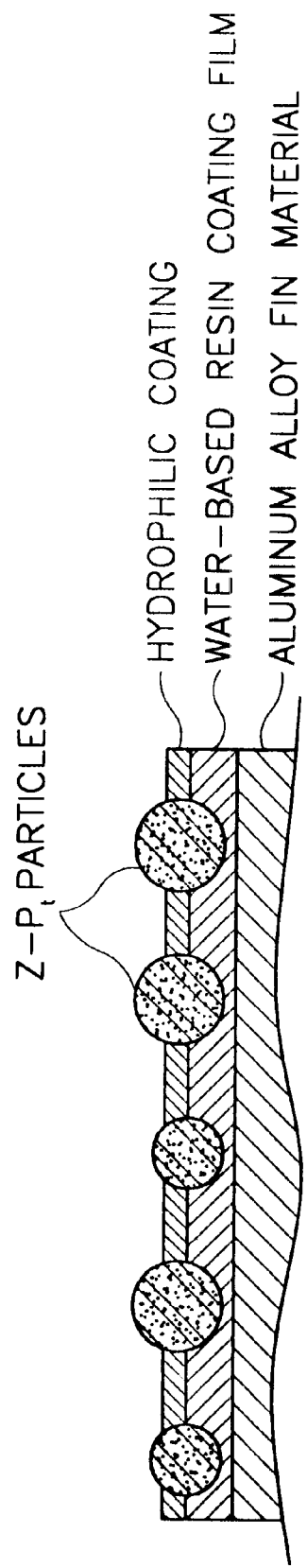
FIG. 1 is a magnified sectional view for illustrating the surfaces of the fin.

To overcome the aforementioned problem, the inventors have first selected the most suitable antibacterial and antifungal agents. Since the process of manufacturing pre-coated fin for a heat exchanger includes a heating-drying step in which the corrosion resistant and hydrophilic coating process is conducted on a fin coil, such antibacterial and antifungal agents that are stable and resistant against heating need to be selected. Moreover, since the air flows directly into a room after contacting the heat exchanger fins for air conditioner, such antibacterial and antifungal agents that are not harmful to the human body need to be selected.

A wide range of studies on such antibacterial and antifungal agents has revealed that bis-(2-pyridylthio)-zinc-1,1'-dioxide(hereinafter referred to as, "Z—Pt") is usable. That is, Z—Pt is so safe to the human body that it has been used as raw material for shampoo for human, and so heat-resistant that its weight reduction rate is less than 1% under the baking drying circumstance for forming a hydrophilic coating, i.e., at 230° C. in 30 minutes.

The inventors have studied a method to obtain aluminum alloy fin material having a high hydrophilic property as well as high antibacterial and antifungal properties, and revealed that the above properties can be retained for a long period when a hydrophilic coating is formed by using hydrophilic coating system after formation of water-based resin coating film on the surface of aluminum-alloy fin material using water-soluble resin paint in which Z—Pt is dispersed. In other words, it can be considered that with insoluble Z—Pt particles whose diameters are larger than the thickness of the water-based resin coating film plus the hydrophilic coating, the sectional structure can be so formed as shown in FIG. 1, and the coexistence of the hydrophilic coating and Z—Pt on the same surface can render the hydrophilic property and the antibacterial and antifungal properties to be retained for a long period of time.

Our continuous studies based upon the aforementioned idea revealed that the hydrophilic property and the antibacterial and antifungal properties can be retained for a long period by first forming a resin coating film in an average dry thickness of 0.8–2.2 $\mu$m with (I) a water-soluble resin paint containing Z—Pt particles(A) by 1–30 wt % for the total solid of the paint, with more than 40vol % of said particles being 1–10 $\mu$m in diameter, and second a hydrophilic coating film in an average dry thickness of 0.1–0.6 $\mu$m, In this case, the average thickness of coating film formed by water-based resin paint and hydrophilic coating agent was defined as having to be less than 3 $\mu$m so that part of Z—Pt particle may be exposed outside of the surface.

Further, the inventors have found that high hydrophilic property and high antibacterial and antifungal properties can be retained for a long period by particularly specifying the composition of the hydrophilic coating agent, That is, the present invention relates to an aluminum-alloy fin material with excellent antibacterial and antifungal properties, having two coated films which comprise: (i) a coated film in average dry thickness of 0.8–2.2 $\mu$m, which is first formed by treating (I) a water-soluble resin paint containing 1–30 wt % of (A) bis-(2-pyridilthio)-zinc-1,1'-dioxide particles among the total solids of the paint, with 40 or more vol % of said particles being 1–10 $\mu$m in diameter; and (ii) a coated film in average dry thickness of 0.1–0.6 $\mu$m, which is formed thereafter by treating (II) a mixed aqueous solution containing (P1) vinyl resin with secondary alcoholic structure or derivative thereof, (P2) water soluble acrylic resin with sulfonic acid group or salt thereof and (B) water block isocyanate compound, in the range of (P1):(P2)=1:8 or in the range of ((P1)+(P2)):(B)=94:6 to 86:14 in wt % for solids; an aluminum-alloy fin material that said aqueous solution (II) further comprises antibacterial and antifungal agent able to be mixed therewith; and a heat exchanger for air conditioner, provided with such aluminum-alloy fin materials.

As for Z—Pt used in the invention, one of the examples is "Zinc Omazine"(by Olin) which needs to be dispersed in water for use, and a ready-made water dispersion system can be also available. Z—Pt is, however, required to contain 40 vol % or more of particles within the range of 1–10 $\mu$m in diameter. Short of meeting the requirement, the exposure degree of the Z—Pt particles becomes inappropriate. That is, the particles, each smaller than 1 $\mu$m are buried under the coating, so that they cannot exhibit their effects. On the other hand, the particles, each bigger than 10 $\mu$m are readily to fall out of the coating and thus the sustaining power of the antibacterial and antifungal properties are diminished. For this reason, it is required to contain more than 40 vol % of particles within the range of 1–10 $\mu$m in diameters.

In addition, the content Z—Pt needs to be within 1–30 wt % among the total solids. When the content is less than 1 wt %, the antibacterial and antifungal effects are not sufficient. When the contents are more than 30 wt %, the proportion of Z—Pt existing on the surface rises, which entails the deterioration of the corrosion resistance as well as hydrophilic property. The range of 3–20 wt % is more preferable.

And, water based resin to blend with Z—Pt particle can be used as the resin component in water-based resin coating agent (I) before and after the formation of coating, and more particularly, water emulsions or dispersions of acrylic, urethane, epoxy and polyethylene are used. Further, not only bridging agents such as melanin, epoxy and isocyanate which are able to bridge the above component, but also a surface active agent and a high boiling point solvent, for the improved uniformity of the coating, can be added.

Still further, the average thickness of the coating film formed with the aforementioned water-based resin paint (I) needs to be within 0.8–2.2 $\mu$m. When the average thickness is under 0.8 $\mu$m, the corrosion resistance is not sufficient and Z—Pt is subject to fall-out. When the average thickness is beyond 2.2 $\mu$m, the heat exchange efficiency of the fin material is readily deteriorated. More preferable range is therefore 1.0–1.8 $\mu$m.

The following is the explanation about a mixed aqueous solution (II) of the present invention.

Vinyl resin with secondary alcoholic structure or water soluble derivative thereof (P1) is a polymer with the general formula as represented below, which can be vinyl acetate or its copolymer, or a water soluble polymer obtained by reacting them.

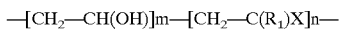

wherein $R_1$ is H or $CH_3$.

X represents many kinds of ionic substitutional group and the number of its kinds can be more than two. When m+n=100, m is 50–100, preferably 60–100, more preferably 70–100.

The water soluble polymers with the above formula is, for example, a hydrolyzed homopolymer of vinyl acetate, commercially available as PVA.

It is a polymer which can be represented by the following structure

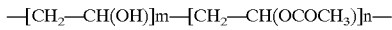

and classified by the degree of hydrolysis.

m=99~100 completely saponified
m=90~99 almost saponified
m<70 partially saponified The PVA derivates generally include anion denatured PVA, cation denatured PVA and active methylene denatured PVA, while the main point is that it (P1), as well as P2 and B, is water-soluble and have the structure of the above general formula. Anion denatured PVA can be, for example, acrylic acid, methacrylic acid, maleic anhydride, vinyl sulfonic acid, methacryloxyethylphosphate or acrylic ester, or can be a hydrolized copolymer from vinyl acetate and monomer which contains carboxylic group, sulfonic acid group or phosphoric acid group, or can be sulfonic acid ester or phosphoric acid ester of PVA.

As the active methylene denatured PVA, a reaction product of PVA and diketen or something like that is known. It is, of course, possible to use styrene, acrylonitrile, vinyl ether or nonionic polymeric monomer as a copolymeric monomer to such a degree that the water solubility may not be restricted. Further, a copolymer of vinyl acetate and 2 or more kinds of the above polymeric monomers can be used. The molecular weight of (P1) is preferably more than 5,000, and in case of less than 5,000, high hydrophilic and water-insoluble, the proportion of bridging agent needs to be raised.

The explanation about water soluble acrylic resin containing sulfonic acid group and/or salts thereof (P2) will be followed. The monomer containing sulfonic acid group includes vinyl sulfonic acid, sulfoethyl acrylate, sulfoethlmethacrylate, N-methylenesulfonicacid acrylate, 2-acrylamide-2-methylsulfonic acid, styrene sulfonic acid, etc. or salts thereof, and polymer or copolymer from the these monomers can be used for water soluble acrylic resin (P2).

In case of copolymer, in order to achieve the object of this invention, the amount of nonionic monomer such as styrene, (meth) acrylic acid ester, vinyl acetate, etc., in the copolymer is less than 40 mol %, preferably less than 20 mol %. In addition, a monomer such as acid halide, which can be polymerized to a polymer such as poly(meth) acrylic acid chloride that can be hydrolized to a poly(math) acrylic acid. The molecular weight of (P2) is more than 1,000, preferably more than 3,000.

As a water block cyanate compound(B), polyisocyanate blocked with NaHSO3 can be used and the amount used depends on the structure. The amount used is generally 1–400 parts by weight, preferably 5–200 parts by weight, more preferably 10–100 parts by weight, to the 100 parts by weight of PVA polymer (P1).

When a coating is formed with a mixed solution (II), the dry coat thickness needs to be in the range of 0.1–0.6 $\mu$m. Under 0.1 $\mu$m, the hydrophilic property is not sufficient. Beyond 0.6 $\mu$m, the heat exchange efficiency of the fin material is readily lowered due to the summed thickness of the coated film. More preferable range is 0.2–0.5 $\mu$m.

Further, for the improved antifungal effect of Z—Pt particles, it is possible to add a known antifungal agent which can be mixed with the particles, into the mixed solution (II).

The explanation about the method to prepare the aluminum-alloy fin material of this invention will be followed. The aluminum-alloy fin material surface, which is washed by a solvent-based cleanser, or an alkali or acidic water-based cleanser, is treated with spray, dipping, roll coat, shower coat, etc., in order, using the water-based resin painting (I) and the mixed solution (II). Further, the aluminum-alloy fin material can be treated in advance with chromate, zinc phosphate, titanium phosphate, zirconum phosphate, etc., in order to improve the corrosion resistance, the adherence, etc.

The treatment by water-based paint (I) containing insoluble Z—Pt particle is preferably accompanied by agitating, since it can keep the dispersed state of Z—Pt uniform and thus the antibacterial and antifungal properties can be more easily exhibited. Further, the temperature of the fin material heated is preferably under 230° C., in view of heat stability. It is the same with the case of treatment by the mixed solution (II).

With the constitution as described above, the aluminum alloy fin material of the present invention comes to obtain excellent antibacterial and antifungal properties due to the Z—Pt particles partially exposed on the surface, and since the particles are supported by the water-based resin coating film, the particles are hardly damaged by dew and can exert their effects for a long time. Moreover, since the specified content of Z—Pt particles guarantee the proportion of hydrophilic coating film on the surface, high hydrophilic property can be retained for a long period of time.

The invention is illustrated in more detail by reference to the following examples. It will be appreciated however, that modification may be made in our invention.

The test method used in examples and the comparative examples are as follows.

1. Water-based Resin Paint (I) and a Mixed Aqueous Solution (II)

Table. 1 shows the contents of the water-based resin paint used in the examples and the comparative examples.

"Partope TD208D"(acrylalkylesterstylene copolymer paint, 26.5 wt %) by Japan PARKERIZING CO. LTD. was a base where antibacterial and antifungal agent were added under the conditions as described in Table 1.

TABLE 1

| | | mixing proportion | | |
|---|---|---|---|---|
| | | water-based resin paint (*1) (wt % of solids) | Z-Pt (wt % of solids) | condition of Z-Pt used |
| composition of the invention | a | 97 | 2 | unprocessed Z-Pt(*2) |
| | b | 90 | 10 | " |
| | c | 85 | 15 | " |
| | d | 80 | 20 | " |
| | e | 75 | 25 | " |
| | f | 70 | 30 | " |
| | g | 75 | 25 | grinded Z-Pt(*2) with 40 vol % particles of 1–10 $\mu$m in size(*3) |
| composition of the comparative examples | h | 75 | 25 | grinded Z-Pt(*2) with 40 vol % particles of 1–10 $\mu$m in size(*3) |
| | i | 75 | 25 | Z-Pt(*2) solublized by PEG400 |
| | j | 99.5 | 0.5 | unprocessed Z-Pt(*2) |
| | k | 66 | 35 | unprocessed Z-Pt(*2) |

(*1)'Partope TD208D"(Japan PARKERIZING CO. LTD) was used
(*2)Olin "Zinc Omazine"(about 50% of particles with 1–10 $\mu$m in thickness)
(*3)The size and distribution of the particles are determined with Particle size analyzer LA-700 (HORIBA).

The table 2 shows the contents of the mixed aqueous solution used in the examples and comparative examples.

TABLE 2

| | | P1 | solids (wt %) | P2 | solids (wt %) | B: solids (wt %) | antifungal agent (wt %) |
|---|---|---|---|---|---|---|---|
| The invention | (a) | P1-a | 34 | P2-a | 60 | 6 | — |
| | (b) | P1-b | 14 | P2-c | 80 | 6 | — |
| | (c) | P1-c | 40 | P2-c | 50 | 10 | — |
| | (d) | P1-a | 10 | P2-b | 78 | 12 | — |
| | (e) | P1-b | 30 | P2-a | 61 | 9 | — |
| | (f) | P1-c | 20 | P2-b | 71 | 9 | — |
| | (g) | P1-a | 30 | P2-b | 60 | 6 | 4 |

TABLE 2-continued

|  |  | P1 | solids (wt %) | P2 | solids (wt %) | B: solids (wt %) | antifungal agent (wt %) |
|---|---|---|---|---|---|---|---|
| comparative examples | (h) | — | 0 | P2-c | 89 | 11 | — |
|  | (i) | P1-b | 88 | — | 0 | 12 | — |
|  | (j) | P1-c | 30 | P2-b | 70 | 0 | — |
|  | (k) | P1-c | 38 | PAA | 60 | 12 | — |

P1-a: saponification degree 90 mol % polyvinylalcohol, molecular weight about 100,000.
P1-b: diketen-treated polyvinylalcohol, molecular weight about 50,000.
P1-c: 3 mol % of sulfonic acid contained polyvinylalcohol, molecula weight about 20,000.
P2-a: 20 mol % sulfonethylacrylate·acrylic acid copolymer, molecular weight about 4,000
P2-b: 30 mol % sulfonethylacrylate·acrylic acid copolymer, molecular weight about 80,000
P2-c: 40 mol % sulfonethylacrylate·acrylic acid copolymer, molecular weight about 80,000
PAA: polyacrylic acid, molecular weight about 50,000
B: zincate block·polyethyl isocyanate prepolymer(NCO: about 5%)
antifungal agent: 2-methyl-4-isothiazolin-3-on 2. Method of Forming a Coating Film on the Fin Material 1) Test Piece and its Pre-treatment JIS-A1100 aluminum alloy material test pieces(0.11 mm in fin thickness), which are commercially available, are pre-treated in the manner as follows.

A) Removal of Fat and Drying
a. removal of fat: using "fin cleaner 4498SK"(Japan Parkerizing co. ltd) at 55° C., for 10 seconds in spray manner.
b. water cleansing: using service water, 15 seconds of spray water cleaning.
c. drying: in the electric oven at 80° C. in 5 minutes.

B) Removal of Fat, Chromating and Drying
a. removal of fat: at 55° C., spraying for 10 sec using "fin cleaner 4498SK"(Japan PARKERIZING CO. LTD)
b. water cleaning: 15 seconds of spray water cleaning using service water,
c. chromate process: at 55° C., spraying for 7 sec using "archrome K-702"(Japan Parkerizing co. ltd), followed by treating chromate of 15±5 mg/m² in Cr adhesion on surface
d. drying: at 80° C. in 5 minutes, in electric oven 2) Coated Film Forming Method Using water-based paint (I) in table 1 and a mixed aqueous solution (II) in table 2, the pre-treated test pieces (A or B) underwent the following method. The kinds of test pieces and water-based resin paints (I) and mixed aqueous solutions (II) and the respective average dry coat thicknesses are shown in table 3.

TABLE 3

| test piece | water-based resin paint | average dry coat thickness (μm) | mixed aqueous solution (II) | average dry coat thickness (μm) |
|---|---|---|---|---|
| example |  |  |  |  |
| 1 | A | a | 0.8 | (a) | 0.6 |
| 2 | A | b | 1.0 | (b) | 0.5 |
| 3 | A | c | 1.2 | (c) | 0.4 |

TABLE 3-continued

| test piece | water-based resin paint | average dry coat thickness (μm) | mixed aqueous solution (II) | average dry coat thickness (μm) |
|---|---|---|---|---|
| 4 | A | d | 1.4 | (d) | 0.3 |
| 5 | A | e | 1.8 | (e) | 0.2 |
| 6 | B | f | 2.2 | (f) | 0.1 |
| 7 | A | g | 1.2 | (f) | 0.4 |
| 8 | B | a | 1.2 | (g) | 0.4 |
| comparative example |  |  |  |  |
| 1 | A | h | 1.5 | (b) | 0.2 |
| 2 | B | i | 1.3 | (d) | 0.3 |
| 3 | B | j | 1.8 | (e) | 0.2 |
| 4 | A | k | 0.8 | (f) | 0.4 |
| 5 | A | a | 1.3 | (h) | 0.3 |
| 6 | B | b | 1.2 | (i) | 0.3 |
| 7 | B | c | 1.0 | (j) | 0.4 |
| 8 | B | f | 1.5 | (k) | 0.3 |
| 9 | B | a | 0.5 | (a) | 0.1 |

① application of aqueous solution resin paint (I): applying it by way of roll-coating manner until the desired average dry coat thickness is obtained,
② baking drying: baking in an electric oven at 200° C. for 1 minute.
③ cooling: cooling the test piece so that the temperature thereof falls under 40° C.
④ appliction of the mixed aqueous solution (II): applying it by way of roll-coating manner until the desired average dry coat thickness is obtained,
⑤ baking drying: baking in an electric oven at 230° C. for 1 minute.
⑥ cooling: cooling the test piece so that the temperature thereof falls under 40° C.

3. Test Method

1) Test of the Persistency of the Hydrophilic Property.

The test pieces were deposited in running water for 8 hours and then dried at 80° C. in 16 hours, steps of which were repeated 5 times. Then, the contact angles to water were determined by using a FACE contact angle measuring instrument CA-X type(Kyowa Kaimen Kagaku).

2) Antibacterial Property Test

The respective test pieces were cut in 3×3 cm, and centrally put on the sterilized petri dish. Then, an absorption paper was cut to the same size as the test piece, sterilized (120° C.×3 hours) by drying and heating and put on the test piece. The 1.0 ml paper was then inoculated with bacteria solution and cultivated in a hot tube settled to 28±2° C. for 24 hours, where the change of the number of the survived bacteria. The bacteria solution was prepared by cultivating *Escherichiacoli* and *Staphylococcus aureus* in beef stock culture fluid(prepared by dissolving beef stock 5 g, peptone 10 g and sodium chloride 5 g in 1 l distilled water and sterilizing it in the autoclave of 121° C.×15 min) and settling the number of bacteria to about $10^6$ (number/ml).

For determinating the number of survived bacteria, the sample was diluted with saline solution to 10, $10^2 \sim 10^4$ times in order, then injected to petri dishes by 1 ml respectively, and then beef stock agar medium (prepared by dissolving beef stock 5 g, peptone 10 g, sodium chloride 5 g and agar 15 g in 1 l distilled water and sterilizing it in 121° C.×15 min autoclave) was added to the dishes, agitated and left for some period. When the medium was solidified, the dishes were agitated and put into a thermostat, where the bacteria were cultured for 2 weeks, and the numbers of colony of the bacteria were counted 3) Antifungal Property Test The test pieces were set on the middle of the inorganic salt plate medium (prepared by dissolving sodium nitrate 2 g, potassium phosphate 0.7 g, potassium phosphate (II) 0.3 g, magnesium sulfate 7 hydrate 0.5 g, potassium chloride 0.5 g, ferrous sulfate 7 hydrate 0.01 g, grape sugar 30 g and agar 20 g into 1 l distilled water and then sterilizing it in the autoclave of 121° C.×15 min) and mixed spore suspension (prepared by sterilizing a composition in 100 ml trigonal flask, which consists of sodium nitrate 2 g, potassium phosphate 0:7 g, potassium phosphate(II) 0.3 g, magnesium sulfate 7 hydrate 0.5 g, potassium chloride 0.5 g, ferrous sulfate 7 hydrate 0.01 g, grape sugar 30 g and distilled water 1L in 121° C.×15 min autoclave, then adding respective 100 spores of *Aspergillus niger, Chaetomium globosum, Paecilomyces variotii, Penicillum funiculosum* and *Trichoderma viride* therein, then dispersing filtering by dried and sterilized filter) are uniformly wrapped on the surface by 1 ml and put into a thermostat settled to 28±2° C. where the fungi were cultured for 4 weeks, and then the growth states were analyzed by the following standards.

0: Mold is not visible on the sample surface through a microscope of 50 magnification.
1: The growth of mold on the sample surface is not appreciated with the naked eye
2: The growth of mold is not appreciated on less than 25% of sample surface.
3: The growth of mold is not appreciated on 25–50% of the sample surface
4: The growth of mold is not appreciated on 50–100% of the sample surface.
5: The whole surface of the sample are coved with mold.

The results of the tests are shown in table 4.

TABLE 4

|  | test of persistency of the hydrophilic property | antibacterial property | | antifungal property |
|---|---|---|---|---|
|  |  | E. coli | S. aureus | test |
| example 1 | 15~25° | 99.6% | 99.9% | 2 |
| example 2 | 10~20° | 99.5% | 99.9% | 2 |
| example 3 | 10~20° | 99.9% | 99.9% | 1 |
| example 4 | 10~20° | 99.7% | 99.9% | 2 |
| example 5 | 15~25° | 99.1% | 99.9% | 1 |
| example 6 | 20~30° | 99.9% | 99.9% | 1 |
| example 7 | 10~20° | 99.2% | 99.9% | 2 |
| example 8 | 15~25° | 99.8% | 99.9% | 0 |
| comparative example 1 | 10~20° | 68.1% | 97.5% | 4 |
| comparative example 2 | 10~20° | 58.7% | 96.1% | 4 |
| comparative example 3 | 15~25° | 45.0% | 88.8% | 4 |
| comparative example 4 | 30~40° | 99.9% | 99.9% | 1 |
| comparative example 5 | 70~80° | 99.8% | 99.9% | 2 |
| comparative example 6 | 45~55° | 90.3% | 99.9% | 2 |
| comparative example 7 | 70~80° | 99.9% | 99.9% | 2 |
| comparative example 8 | 35~45° | 99.9% | 99.9% | 2 |
| comparative example 9 | 20~30° | 72.0% | 99.9% | 4 |

It is apparently appreciated from the table 4, that the examples 1–8, which correspond to the surface-treated fin material of the invention, have excellent persistency of the hydrophilic property, the antibacterial and antifungal properties, and the air conditioner therewith can retain high hydrophilic property and the antibacterial and antifungal properties for a long time.

On the other hand, in the case of the comparative example 1 which contains 30 vol % of particles with 1–10 µm thickness, a lot of particles with less than 1 µm thickness are buried under the coated film, and thus the antibacterial and antifungal properties are not sufficient. In case of the comparative example 2 where Z—Pt is added after solubilized and thus buried under the coated film, the antibacterial and antifungal properties are not sufficient.

In case of the comparative example 3 where Z—Pt particles are added by 1 wt % or less, the antibacterial and antifungal properties are not sufficient. In case of the comparative example 4 where Z—Pt particles are added by 30 wt % or more, the antibacterial and antifungal properties are sufficient, however the persistency of the hydrophilic property is not sufficient.

In case of the comparative example 5 where P1 is not added to mixed aqueous solution (II) and hydrophilic coating film flows, the persistency of the hydrophilic property is very low.

In case of the comparative example 6 where P2 is not added to mixed aqueous solution (II), and in case of the comparative example 7 where water-based block isocyanate compound is not added to mixed aqueous solution (II) and hydrophilic coated film flows, the persistences of the hydrophilic properties are very low. In case of the comparative example 8 where P2 is replaced with polyacrylic acid without sulfonic acid group, the persistency of the hydrophilic property is low. In case of the comparative example 9 where the average dry coating thickness is less than 0.8 µm, the antibacterial and antifungal properties are not sufficient.

The aluminum-alloy fin material of the present invention is positioned in water-based resin coated film, and Z—Pt particles are partially exposed on the surface, which results in satisfactory antibacterial and antifungal properties. In addition, a specific composition of mixed aqueous solution results in good persistency of the hydrophilic property.

Z—Pt exists as the form of insoluble particle, and can be uniformly mixed with hydrophilic coating, and thus does not lower the persistency of the hydrophilic property. Further, since some parts of the Z—Pt are fixed in the water-based resin coating film, it is not readily dropped and not diffused into the dropped water, and thus can retain the antibacterial and antifungal properties for a long period.

What is claimed is:

1. An aluminum-alloy fin material with antibacterial and antifungal properties, comprising:
   (i) a first film with average dry thickness of 0.8–2.2 microns, comprising a water-soluble resin paint containing 1–30 wt % of (A) bis-(2-pyridylthio)-zinc-1,1'-dioxide particles of the total solids in the composition of the paint, 40 or more vol % of said bis-(2-pyridylthio)-zinc-1,1'-dioxide particles being 1–10 microns in diameter;
   (ii) a second film with average dry thickness of 0.1–0.6 microns, formed on the first film, said second film comprising a mixed aqueous solution which comprises (P1) vinyl resin with secondary alcoholic structure or derivative thereof, (P2) a water soluble acrylic resin with sulfonic acid group or salt(s) thereof and (B) water block isocyariate compound, in the range of (P1):(P2)= 1:8 by weight for solids or in the range of ((P1)+(P2)): (B)=94:6 to 86:14 by wt % for solids.

2. The aluminum-alloy fin material as defined in claim 1, wherein said aqueous solution further comprises antibacterial and antifungal agents able to be mixed with said aqueous solution.

3. The aluminum-alloy fin material as defined in claim 1, said aluminum alloy fin material acting as a heat exchanger for an air conditioner.

* * * * *